United States Patent
Awazu et al.

(10) Patent No.: US 9,629,360 B2
(45) Date of Patent: Apr. 25, 2017

(54) WATER-BASED PESTICIDAL SUSPENSION

(75) Inventors: Takao Awazu, Kusatsu (JP); Mitsuo Sano, Kusatsu (JP); Akira Nakagawa, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 943 days.

(21) Appl. No.: 13/808,218

(22) PCT Filed: Jul. 5, 2011

(86) PCT No.: PCT/JP2011/065747
§ 371 (c)(1),
(2), (4) Date: Mar. 7, 2013

(87) PCT Pub. No.: WO2012/005371
PCT Pub. Date: Jan. 12, 2012

(65) Prior Publication Data
US 2013/0171226 A1  Jul. 4, 2013

(30) Foreign Application Priority Data
Jul. 9, 2010 (JP) ................................. 2010-157295

(51) Int. Cl.
| | | |
|---|---|---|
| *A01N 25/30* | (2006.01) | |
| *A01N 25/04* | (2006.01) | |
| *A01N 43/40* | (2006.01) | |
| *A01P 7/04* | (2006.01) | |
| *A01P 3/00* | (2006.01) | |

(52) U.S. Cl.
CPC .............. *A01N 25/30* (2013.01); *A01N 25/04* (2013.01)

(58) Field of Classification Search
CPC ................................ A01N 25/30; A01N 25/04
See application file for complete search history.

(56) References Cited

U.S. PATENT DOCUMENTS

| | | | | |
|---|---|---|---|---|
| 4,824,590 | A * | 4/1989 | Roselle .............. | C11D 17/0013 510/221 |
| 4,932,993 | A * | 6/1990 | Burnell .................... | C05B 7/00 423/305 |
| 2004/0024026 | A1 | 2/2004 | Morita et al. | |
| 2007/0142439 | A1 | 6/2007 | Morita et al. | |
| 2008/0032890 | A1* | 2/2008 | Jensen .................. | A01N 25/14 504/105 |
| 2008/0213326 | A1* | 9/2008 | Amrhein ................ | A01N 25/04 424/405 |
| 2010/0197739 | A1* | 8/2010 | Dexter .................. | A01N 43/40 514/343 |
| 2011/0028521 | A1* | 2/2011 | Morita ................... | A01N 43/40 514/355 |
| 2011/0166022 | A1 | 7/2011 | Israels et al. | |

FOREIGN PATENT DOCUMENTS

| | | | |
|---|---|---|---|
| CA | 2 335 832 | A1 | 12/1999 |
| CN | 101897341 | A | 12/2010 |
| CN | 101946795 | A | 1/2011 |
| DE | 10 2007 013 363 | A1 | 9/2008 |
| DE | 10 2007 013360 | | 9/2008 |
| EP | 0 029 626 | A1 | 6/1981 |
| EP | 0 580 374 | | 1/1996 |
| EP | 1 908 347 | | 4/2008 |
| EP | 2 303 007 | | 4/2011 |
| JP | 1-168604 | | 7/1989 |
| JP | 5-179008 | | 7/1993 |
| JP | 2002-201102 | | 7/2002 |
| JP | 2005-53795 | | 3/2005 |
| JP | 2008-540654 | | 11/2008 |
| JP | 2010-506946 | | 3/2010 |
| JP | 2011 057614 | | 3/2011 |
| WO | WO 1999/66792 | | 12/1999 |
| WO | 02 34050 | | 5/2002 |
| WO | WO 2008067058 | A2 * | 6/2008 ............. A01N 43/40 |
| WO | WO 2008069990 | A1 * | 6/2008 ............. A01N 41/02 |
| WO | 2009 021985 | | 2/2009 |
| WO | WO 2009128409 | A1 * | 10/2009 ............. A01N 43/40 |

OTHER PUBLICATIONS

Kostrosol (CWK Chemiewerk Bad Kostritz GmbH, downloaded from http://www.cwk-bk.de/www/cwken/produkte/kieselsaeure/g5ffnpy6/ on Jul. 15, 2016.*
Sokalan CP 9 (BASF, downloaded from http://www.ptdju.com/resources/external/65D3886E-4434-4D8A-9088-CFE2C29E4C7F/Paint/Water%20Based/Polymeric%20Dispersing/Brochures/Sokalan_CP9.pdf on Jul. 15, 2016.*
Combined Office Action and Search Report issued Oct. 10, 2013 in Chinese Patent Application No. 201180040278.6 with English translation of categories of cited documents.
Office Action issued Feb. 17, 2015 in Japanese Patent Application No. 2011-148010 (English translation).
International Search Report Issued Oct. 6, 2011 in PCT/JP11/065747 Filed Jul. 5, 2011.

* cited by examiner

Primary Examiner — Kortney L Klinkel
Assistant Examiner — Lisbeth C Robinson
(74) Attorney, Agent, or Firm — Oblon, McClelland, Maier & Neustadt, L.L.P.

(57) ABSTRACT

A water-based pesticidal suspension comprises (a) flonicamid, (b) a polycarboxylate surfactant, (c) a sulfonate surfactant, and (d) water. The sulfonate surfactant (c) is at least one member selected from the group consisting of an alkyl sulfosuccinate, a lignosulfonate, a $C_{8-18}$ alkyl benzene sulfonate and a $C_{8-18}$ alkyl diphenyl ether disulfonate. An average particle size of the volume distribution of (a) flonicamid is preferably from 0.5 μm to 10 μm. The polycarboxylate surfactant (b) is preferably a sodium salt of maleic acid/olefin copolymer.

13 Claims, No Drawings

WATER-BASED PESTICIDAL SUSPENSION

TECHNICAL FIELD

The present invention relates to a water-based pesticidal suspension containing, as an active ingredient, an agricultural chemical having a high aqueous solubility, particularly an agricultural chemical having an aqueous solubility of from 500 mg/L to 6,000 mg/L at 20° C.

BACKGROUND ART

A compound having a high aqueous solubility, generally a compound having an aqueous solubility exceeding 100 mg/L at 20° C., is considered to be hardly formulated into a water-based suspension. Especially when a compound having an aqueous solubility exceeding 500 mg/L at 20° C. is employed, a problem is likely to be result with respect to the physicochemical aspect of the formulation in many cases. For example, N-cyanomethyl-4-(trifluoromethyl)nicotinamide (common name: flonicamid) is a compound disclosed as Compound No. 1 in Patent Document 1, and its aqueous solubility at 20° C. is 5,200 mg/L, but in Patent Document 1, no Example is given to formulate flonicamid into a water-based suspension formulation.

Patent Document 2 discloses a pesticidal composition comprising a pyridine type compound and another pesticide, and in its Formulation Example 5, a water-based suspension containing flonicamid is disclosed. However, a water-based pesticidal suspension which employs specific surfactants as in the present invention and which exhibits an excellent physicochemical performance, is not disclosed.

PRIOR ART DOCUMENTS

Patent Documents

Patent Document 1: EP-580374 B
Patent Document 2: WO2002/034050

DISCLOSURE OF INVENTION

Technical Problem

If a water-based pesticidal suspension containing, as an active ingredient, an agricultural chemical having a high aqueous solubility is stored for a long period of time, the dissolved active ingredient undergoes crystallization with suspended particles serving as nuclei, whereby the particles will grow and become coarse, and a stably suspended composition is hardly obtainable. From such a problem in e.g. stability, it is not proper to select water as a dispersant at the time of formulating an agricultural chemical having a high aqueous solubility into a formulation. Further, the growth and coarsening of the active ingredient particles are also influential over deterioration of the pesticidal effects. However, a pesticide formulation using water as a dispersant is very advantageous as it is less susceptible to restrictions in the production, transportation, storage or use from the viewpoint of e.g. the flame point, in handling, as compared with one using an organic solvent as a dispersant. Accordingly, a water-based pesticidal suspension has been desired whereby the growth and coarsening of the active ingredient particles are suppressed while using water as a dispersant.

Solution to Problem

The present inventors have conducted a research to solve the above problem and as a result, have found that by dispersing an agricultural chemical having a high aqueous solubility, particularly agricultural chemical particles having an aqueous solubility of at least 500 mg/L at 20° C., in an aqueous medium containing a polycarboxylate type surfactant and a sulfonate type surfactant, a stable water-based pesticidal suspension free from the growth and coarsening of the active ingredient particles, can be obtained. The present invention has been accomplished on the basis of this discovery. That is, the present invention relates to a water-based pesticidal suspension comprising an agricultural chemical having a high aqueous solubility, particularly an agricultural chemical having an aqueous solubility of at least 500 mg/L at 20° C., a polycarboxylate type surfactant, a sulfonate type surfactant and water. Particularly, the present invention relates to a water-based pesticidal suspension comprising (a) an agricultural chemical or its salt having an aqueous solubility of from 500 mg/L to 6,000 mg/L at 20° C., (b) a polycarboxylate type surfactant, (c) a sulfonate type surfactant, and (d) water.

Advantageous Effect of Invention

According to the present invention, it is possible to prevent the growth and coarsening of the active ingredient particles in the water-based pesticidal suspension during its storage. Accordingly, the water-based pesticidal suspension of the present invention is expected to provide an excellent physicochemical performance and a high pesticidal effect which is stable over a long period of time.

DESCRIPTION OF EMBODIMENTS

In the water-based pesticidal suspension of the present invention (hereinafter referred to simply as the suspension of the present invention), as the agricultural chemical, an agricultural chemical having a high aqueous solubility, particularly an agricultural chemical having an aqueous solubility of from 500 mg/L to 6,000 mg/L at 20° C., is employed, and more preferably, an agricultural chemical having an aqueous solubility of from 3,000 mg/L to 6,000 mg/L at 20° C. is employed. Its specific examples include azamethiphos (aqueous solubility: 1100 mg/L (20° C.)), dazomet (aqueous solubility: 3500 mg/L (20° C.)), pyroquilon (aqueous solubility: 4000 mg/L (20° C.)), pirimicarb (aqueous solubility: 3100 mg/L (20° C.)), thiamethoxam (aqueous solubility: 4100 mg/L (25° C.)), flonicamid (aqueous solubility: 5200 mg/L (20° C.)), etc. Among them, preferred are pirimicarb, thiamethoxam and flonicamid, and more preferred is flonicamid.

The agricultural chemical in the suspension of the present invention may form a salt together with an acidic substance or basic substance. As a salt with an acidic substance, an inorganic acid salt such as a hydrochlorate, a hydrobromate, a phosphate, a sulfate or a nitrate may be mentioned, and as a salt with a basic substance, an inorganic or organic base salt such as a sodium salt, a potassium salt, a calcium salt, an ammonium salt or a dimethylamine salt may be mentioned.

The content of the agricultural chemical in the suspension of the present invention is usually from 0.1 to 90 wt %, preferably from 1 to 60 wt %, more preferably from 5 to 45 wt %.

The polycarboxylate type surfactant may, for example, be polyacrylic acid, polymethacrylic acid, polymaleic acid, polymaleic anhydride, a copolymer of maleic acid or maleic anhydride with an olefin (such as isobutylene or diisobutylene), a copolymer of acrylic acid and itaconic acid, a copolymer of methacrylic acid and itaconic acid, a copolymer of maleic acid or maleic anhydride with styrene, a copolymer of acrylic acid and methacrylic acid, a copolymer of acrylic acid and methyl acrylate, a copolymer of acrylic acid and vinyl acetate, a copolymer of maleic acid or maleic anhydride with acrylic acid, an N-methyl-fatty acid (e.g. $C_{8-18}$) sarcosinate, a carboxylic acid such as a resin acid or a fatty acid (e.g. $C_{8-18}$), or a salt of such a carboxylic acid. Such a salt may, for example, be an alkali metal (such as sodium or potassium), an alkaline earth metal (such as calcium or magnesium), ammonium or various amines (such as an alkylamine, a cycloalkylamine and an alkanolamine). Further, a commercially available polycarboxylate may be used as it is, and for example, Geropon T/36 (sodium salt of maleic acid/olefin copolymer, tradename of Rhodia) may be mentioned.

The content of the polycarboxylate type surfactant in the suspension of the present invention may be optionally changed depending upon the amount of the active ingredient compound to be added. However, it is usually from 0.1 to 20 wt %, preferably from 0.1 to 10 wt %. The weight ratio in content of the active ingredient to the polycarboxylate type surfactant is usually from 1:0.001 to 1:10, preferably from 1:0.005 to 1:2.

The sulfonate type surfactant may, for example, be a lignosulfonate, an alkyl sulfosuccinate, a $C_{8-18}$ alkylbenzene sulfonate or a $C_{8-18}$ alkyl diphenyl ether disulfonate. As such a sulfonate type surfactant, it is preferred to use a lignosulfonate, and it is particularly preferred to use a lignosulfonate and an alkyl sulfosuccinate.

The lignosulfonate may, for example, be calcium lignosulfonate, sodium lignosulfonate, potassium lignosulfonate, magnesium lignosulfonate or ammonium lignosulfonate. For example, New Kargen WG-4 (sodium lignosulfonate, manufactured by TAKEMOTO OIL & FAT Co., LTD.), New Kargen RX-B (sodium lignosulfonate, manufactured by TAKEMOTO OIL & FAT Co., LTD.), SANX P-252 (sodium lignosulfonate, manufactured by NIPPON PAPER CHEMICALS Co., LTD.), SANX C (calcium lignosulfonate, manufactured by NIPPON PAPER CHEMICALS Co., LTD.), SANX P201 (calcium lignosulfonate, manufactured by NIPPON PAPER CHEMICALS Co., LTD.), VANILLEX N (partially desulfonated sodium lignosulfonate, manufactured by NIPPON PAPER CHEMICALS Co., LTD.), or PEARLLEX NP (high molecular weight sodium lignosulfonate, manufactured by NIPPON PAPER CHEMICALS Co., LTD.), may, for example, be mentioned.

The alkyl sulfosuccinate may, for example, be a compound represented by the formula (I):

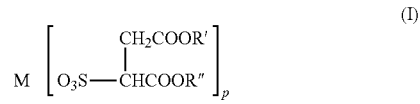

[wherein each of R' and R" which are independent of each other, is a linear or branched $C_{1-12}$ alkyl group; M is Na, Ca or K; when M is Na or K, p is 1; and when M is Ca, p is 2.] Among them, sodium dioctyl sulfosuccinate is preferred. Specific examples of the sodium dioctyl sulfosuccinate include AGNIQUE EHS70WE (manufactured by Cognis), LANKROPOL 4500 (manufactured by LION AKZO Co., Ltd), New Kargen EP-70G (manufactured by TAKEMOTO OIL & FAT Co., LTD.), New Kargen EX-70 (manufactured by TAKEMOTO OIL & FAT Co., LTD.), etc.

The content of the sulfonate type surfactant in the suspension of the present invention may suitably be changed depending upon the amount of the active ingredient compound to be added, but it is usually from 0.1 to 30 wt %, preferably from 0.1 to 20 wt %. The weight ratio in content of the active ingredient to the sulfonate type surfactant is usually from 1:0.001 to 1:20, preferably from 1:0.005 to 1:4. The weight ratio in content of the polycarboxylate type surfactant to the sulfonate type surfactant is usually from 1:0.01 to 1:200, preferably from 1:0.01 to 1:40.

In the suspension of the present invention, water is employed as a dispersant. In the suspension of the present invention, water may be incorporated as the rest of the above-mentioned (a), (b), (c) and the after-mentioned other components to adjust so that the entirety becomes 100 wt %. The content of the water in the suspension of the present invention is usually from 9.8 to 99.7 wt %, preferably from 20 to 98.8 wt %.

To the suspension of the present invention, as other optional components, additives such as an antifreezing agent, a thickener, an antifoaming agent, an antiseptic agent, a dispersant, a wetting agent, a pH modifier, a stabilizer, etc. may suitably be added, as the case requires. As such additives, an antifreezing agent, a thickener, an antifoaming agent, an antiseptic agent, etc. are preferred.

As the antifreezing agent, various ones may be mentioned, but a dihydric alcohol which is effective also as a viscosity lowering agent, is preferred. As the dihydric alcohol, an alkylene glycol such as ethylene glycol or propylene glycol may be mentioned, and it is particularly preferred to employ propylene glycol among them. The amount of the antifreezing agent to be used in the suspension of the present invention is usually from 2 to 30 wt %, preferably from 5 to 10 wt %.

The thickener may, for example, be a natural polysaccharide such as xanthan gum, rhamsan gum, locust bean gum, carrageenan or welan gum; a synthetic polymer such as sodium polyacrylate; a semisynthetic polysaccharide such as carboxy methyl cellulose; a mineral fine powder such as aluminum magnesium silicate, smectite, bentonite, hectorite or fumed silica, or alumina sol. The amount of the thickener to be used in the suspension of the present invention is usually from 0.01 to 5.0 wt %, preferably from 0.05 to 1.0 wt %.

As the antiseptic, various ones may be mentioned, but for example, Proxel GXL (tradename, Zeneca AG) may be used. The amount of the antiseptic to be used in the suspension of the present invention is usually from 0.01 to 1.0 wt %, preferably from 0.05 to 0.2 wt %.

The antifoaming agent is added for the purpose of suppressing formation of bubbles at the time of producing or diluting with water the suspension of the present invention thereby to avoid a trouble during the production or preparation of a diluted suspension. As such an antifoaming agent, a silicone type antifoaming agent containing polydimethylsiloxane as an active ingredient, may be mentioned. For example, Rhodorsil Antifoam 416 (tradename, Rhodia Nicca Ltd.), Rhodorsil Antifoam 481 (tradename, Rhodia Nicca Ltd.), Rhodorsil Antifoam 432 tradename, Rhodia Nicca Ltd.), KM 72 (tradename, Shin-Etsu Chemical Co., Ltd.), KM 75 (tradename, Shin-Etsu Chemical Co., Ltd.), or Anti-mousse (tradename, BELCHIM CROP PROTECTION) may be mentioned. Here, the silicone type antifoaming agent includes an antifoaming agent containing silica. The amount of the antifoaming agent to be used in the suspension of the present invention is usually from 0.01 to 10 wt %, preferably from 0.1 to 1.0 wt %.

The suspension of the present invention can be produced by a usual method for producing a water-based pesticidal suspension. For example, after mixing blend components, wet grinding is carried out to make active ingredient particles fine. The slurry particles thereby obtainable are preferably fine, and the average particle size (volume) of the agricultural chemical of the above (a) is made to be a particle size of from 0.5 to 10 μm, more preferably from 1 to 3 μm, from the viewpoint of the suspension stability in a case where the finally obtainable water-based pesticidal suspension is formulated as a water diluted suspension. Here, the average particle size is one measured by a particle size analyzer Microtrac HRA (manufactured by NIKKISO Co., Ltd.).

At the time of formulating the suspension of the present invention, as the method of wet grinding, bead mill or sand mill may, for example, be mentioned. As bead mill, DYNO-MILL may, for example, be mentioned.

The viscosity of the suspension of the present invention is preferably from 100 to 1000 mPa·S, more preferably from 200 to 500 mPa·S. Here, the viscosity is one measured by a B type viscometer (rotational speed of rotor: 60 rpm (20° C.)).

A method for application of the suspension of the present invention is not particularly limited. However, usually, the suspension of the present invention is prepared as described above, and then a water-diluted liquid suitable for e.g. application by spraying is prepared, and it can be applied to soil, plants, etc. The method for preparing the water-diluted liquid is not particularly limited, and the suspension of the present invention may be added to water in a suitable amount as a diluting liquid, followed by mixing by means of a suitable means. The degree of dilution is not particularly limited, and it is possible to determine the concentration of the water-diluted liquid so that the pesticidal component will be in contact with soil, plants, etc. at a suitable concentration after the application.

The concentration of the suspension of the present invention to be used cannot generally be defined, since it varies depending upon conditions such as the crop plants, the method of use, the type of the formulation, the amount to be applied, etc. However, in the case of foliar treatment, the concentration of the active ingredient is usually from 1 to 50,000 ppm; in the case of water surface application, the concentration of the active ingredient is usually from 50 to 50,000 ppm; and in the case of soil treatment, the concentration of the active ingredient is usually from 1 to 1,000 ppm.

The suspension of the present invention may be used as mixed with or in combination with other agricultural chemicals other than the agricultural chemical of the above (a), as the case requires, for example, an insecticide, a miticide, a nematicide, a soil pesticide, a fungicide, an antivirus agent, an attractant, a herbicide, a plant growth-regulating agent, etc. In such a case, a further superior effect may sometimes be obtainable. In such a case, at the time of preparing the suspension of the present invention, the above (a), (b), (c) and (d), and such other agricultural chemicals may be mixed and formulated together, or they may be separately formulated so that they may be mixed for use at the time of application.

The active ingredient compounds of the insecticide, the miticide, the nematicide or the soil insect pesticide, i.e. insecticidal compounds, in the above-mentioned other agricultural chemicals, include, for example, (by common names, some of them are still in an application stage, or test codes of Japan Plant Protection Association):

organic phosphate compounds, such as profenofos, dichlorvos, fenamiphos, fenitrothion, EPN, diazinon, chlorpyrifos, chlorpyrifos-methyl, acephate, prothiofos, fosthiazate, cadusafos, disulfoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, ESP, azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet, phorate, phoxim and triazophos;

carbamate compounds, such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC and fenothiocarb;

nereistoxin derivatives, such as cartap, thiocyclam, bensultap, thiosultap-sodium thiosultap-disodium, monosultap, bisultap and thiocyclam hydrogen oxalate;

organic chlorine compounds, such as dicofol, tetradifon, endosulfan, dienochlor and dieldrin;

organic metal compounds, such as fenbutatin oxide and cyhexatin;

pyrethroid compounds, such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin, flumethrin and decamethrin;

benzoylurea compounds, such as diflubenzuron, chlorfluazuron, teflubenzuron, flufenoxuron, lufenuron, novaluron, triflumuron, hexaflumuron, bistrifluoron, noviflumuron and fluazuron;

juvenile hormone-like compounds, such as methoprene, pyriproxyfen, fenoxycarb and diofenolan;

pyridazinone compounds, such as pridaben;

pyrazole compounds, such as fenpyroximate, fipronil, tebufenpyrad, ethiprole, tolfenpyrad, acetoprole, pyrafluprole and pyriprole;

neonicotinoids, such as imidacloprid, nitenpyram, acetamiprid, thiacloprid, thiamethoxam, clothianidin, nidinotefuran, dinotefuran and nithiazine;

hydrazine compounds, such as tebufenozide, methoxyfenozide, chromafenozide and halofenozide;

pyridine compounds, such as pyridalyl and flonicamid;

cyclic keto-enol compounds, such as spirodiclofen; spiromesifen and spirotetramat;

strobilurin compounds, such as fluacrypyrim;

pyrimidinamine compounds, such as flufenerim;

dinitro compounds; organic sulfur compounds; urea compounds; triazine compounds; hydrazone compounds;

other compounds, such as buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, propargite, clofentezine, metaflumizone, flubendiamide, cyflumetofen, chlorantraniliprole, cyantraniliprole, cyenopyrafen, pyrifluquinazon, fenazaquin, amidoflumet, sulfluramid, hydramethylnon, metaldehyde, HGW-86, ryanodine, verbutin, 3-bromo-N-(2-bromo-4-chloro-6-(1-cyclopropylethylcarbamoyl)phenyl)-1-(3- chloropyridin-2-yl)-1H-pyrazol-5-carboxamide, 3-bromo-N-(4-chloro-2-(1-cyclopropylethylcarbamoyl)-6-methylphenyl)-1-(3-chloropyridin-2-yl)-1H-pyrazol-5-carboxamide, 3-bromo-N-(2-bromo-4-chloro-6-(cyclopropylmethylcarbamoyl)phenyl)-1-(3-chloropyridin-2-yl)-1H-pyrazol-5-carboxamide, 3-bromo-N-(4-chloro-2-methyl-6-(methylcarbamoyl)phenyl)-1-(3-chloropyridin-2-yl)-1H-pyrazol-5-carboxamide and 3-bromo-1-(3-chloropyridin-2-yl)-N-(4-cyano-2-methyl-6-(methylcarbamoyl)phenyl)-1H-pyrazol-5-carboxamide; and the like. Further, it may be used in combination with or together with microbial agricultural chemicals, such as insecticidal crystal proteins produced by *Bacillus thuringiensis aizawai, Bacillus thuringiensis kurstaki, Bacillus thuringiensis israelensis, Bacillus thuringiensis japonensis, Bacillus thuringiensis tenebrionis* or *Bacillus thuringiensis*, insect viruses, etomopathogenic fungi, and nematophagous fungi; antibiotics or semisynthetic antibiotics, such as avermectin, emamectin benzoate, milbemectin, milbemycin, spinosad, ivermectin, lepimectin, DE-175, abamectin, emamectin and spinetoram; natural products, such as azadirachtin and rotenone; and repellents, such as deet.

The active ingredient compounds of the fungicide, i.e. the fungicidal compounds, in the above-mentioned other agricultural chemicals include, for example, (by common names, some of them are still in an application stage, or test codes of Japan Plant Protection Association):

anilinopyrimidine compounds, such as mepanipyrim, pyrimethanil, cyprodinil and ferimzone;

triazoropyrimidine compounds, such as 5-chloro-7-(4-methylpiperidin-1-yl)-6-(2,4,6-trifluorophenyl)[1,2,4]triazolo[1,5-a]pyrimidine;

pyridinamine compounds, such as fluazinam;

azole compounds, such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole and imibenconazole;

quinoxaline compounds, such as quinomethionate;

dithiocarbamate compounds, such as maneb, zineb, mancozeb, polycarbamate, metiram, propineb and thiram;

organic chlorine compounds, such as fthalide, chlorothalonil and quintozene;

imidazole compounds, such as benomyl, cyazofamid, thiophanate-methyl, carbendazim, thiabendazole and fuberiazole;

cyanoacetamide compounds, such as cymoxanil;

anilide compounds, such as metalaxyl, metalaxyl-M, mefenoxam, oxadixyl, ofurace, benalaxyl, benalaxyl-M (another name: kiralaxyl, chiralaxyl), furalaxyl, cyprofuram, carboxin, oxycarboxin, thifluzamide, boscalid, bixafen, isotianil, tiadinil and sedaxane;

sulfamide compounds, such as dichlofluanid;

copper compounds, such as cupric hydroxide and oxine copper;

isoxazole compounds, such as hymexazol;

organophosphorus compounds, such as fosetyl-Al, tolclofos-methyl, S-benzyl O,O-diisopropylphosphorothioate, O-ethyl S,S-diphenylphosphorodithioate, aluminum ethylhydrogen phosphonate, edifenphos, and iprobenfos;

phthalimide compounds, such as captan, captafol and folpet;

dicarboximide compounds, such as procymidone, iprodione and vinclozolin;

benzanilide compounds, such as flutolanil and mepronil;

amide compounds, such as penthiopyrad, mixture of 3-(difluoromethyl)-1-methyl-N[(1RS,4SR,9SR)-1,2,3,4-tetrahydro-9-isopropyl-1,4-methanonaphthalen-5-yl]pyrazole-4-carboxamide and 3-(difluoromethyl)-1-methyl-N-[(1RS, 4SR,9SR)-1,2,3,4-tetrahydro-9-isopropyl-1,4-methanonaphthalen-5-yl]pyrazole-4-carboxamide (isopyrazam), silthiopham, fenoxanil and furametpyr;

benzamide compounds, such as fluopyram and zoxamide;

piperazine compounds, such as triforine;

pyridine compounds, such as pyrifenox;

carbinol compounds, such as fenarimol;

piperidine compounds, such as fenpropidin;

morpholine compounds, such as fenpropimorph and tridemorph;

organotin compounds, such as fentin hydroxide and fentin acetate;

urea compounds, such as pencycuron;

cinnamic acid compounds, such as dimethomorph and flumorph;

phenylcarbamate compounds, such as diethofencarb;

cyanopyrrole compounds, such as fludioxonil and fenpiclonil;

strobilurin compounds, such as azoxystrobin, kresoximmethyl, metominostrobin, trifloxystrobin, picoxystrobin, oryzastrobin, dimoxystrobin, pyraclostrobin, and fluoxastrobin;

oxazolidinone compounds, such as famoxadone;

thiazolecarboxamide compounds, such as ethaboxam;

valinamide compounds, such as iprovalicarb and benthiavalicarb-isopropyl;

acylamino acid compounds, such as methyl N-(isopropoxycarbonyl)-L-valyl-(3RS)-3-(4-chlorophenyl)-β-alaninate (valiphenalate);

imidazolinone compounds, such as fenamidone;

hydroxyanilide compounds, such as fenhexamid;

benzenesulfonamide compounds, such as flusulfamide;

oxime ether compounds, such as cyflufenamid;

anthraquinone compounds;

crotonic compounds;

antibiotics, such as validamycin, kasugamycin and polyoxins;

guanidine compounds, such as iminoctadine and dodine;

quinoline compounds, such as 6-tert-butyl-8-fluoro-2,3-dimethylquinolin-4-yl acetate (tebufloquin);

thiazolidine compounds, such as (z)-2-(2-fluoro-5-(trifluoromethyl)phenylthio)-2-(3-(2-methoxyphenyl)thiazolidin-2-yliden)acetonitrile (flutianil);

and other compounds, such as pyribencarb, isoprothiolane, pyroquilon, diclomezine, quinoxyfen, propamocarb hydrochloride, chloropicrin, dazomet, metam-sodium, nicobifen, metrafenone, UBF-307, diclocymet, proquinazid, amisulbrom (another name: amibromdole), pyriofenone, mandipropamid, fluopicolide, carpropamid, meptyldinocap, N-[(3',4'-dichloro-1,1-dimethyl)phenacyl]-3-trifluoromethyl-2-pyridine carboxamide, N-[(3',4'-dichloro-1,1-dimethyl)phenacyl]-3-methyl-2-thiophene carboxamide, N-[(3', 4'-dichloro-1,1-dimethyl)phenacyl]-1-methyl-3-trifluoromethyl-4-pyrazole carboxamide, N-[[2'-methyl-4'-(2-propyloxy)-1,1-dimethyl]phenacyl]-3-trifluoromethyl-2-pyridine carboxamide, N-[[2'-methyl-4'-(2-propyloxy)-1,1-dimethyl]phenacyl]-3-methyl-2-thiophene carboxamide, N-[[2'-methyl-4'-(2-propyloxy)-1,1-dimethyl]phenacyl]-1-methyl-3-trifluoromethyl-4-pyrazole carboxamide, N-[[4'-(2-propyloxy)-1,1-dimethyl]phenacyl]-3-trifluoromethyl-2- pyridine carboxamide, N-[[4'-(2 propyloxy)-1,1-dimethyl] phenacyl]-3-methyl-2-thiophene carboxamide, N-[[4'-(2-propyloxy)-1,1-dimethyl]phenacyl]-1-methyl-3-trifluoromethyl-4-pyrazole carboxamide, N-[[2'-methyl-4'-(2-pentyloxy)-1,1-dimethyl]phenacyl]-3-trifluoromethyl-2-pyridine carboxamide, N-[[4'-(2-pentyloxy)-1,1-dimethyl] phenacyl]-3-trifluoromethyl-2-pyridine carboxamide, spiroxamine, S-2188 (fenpyrazamine), S-2200, ZF-9646, BCF-051, BCM-061 and BCM-062.

Among these, preferred as active ingredient compounds to be further incorporated to the suspension of the present invention are the following compounds. These insecticidal compounds or fungicidal compounds are referred to as "compounds of group X".

That is, as the compounds of group X, abamectin, fenobucarb, isoprocarb, chlorfluazuron, chlorpyrifos, fipronil, clothianidin, spinetoram, spinosad, dinotefuran, methoxyfenozide, ethofenprox, ethiprole, acephate, benfuracarb, monocrotophos, silafluofen, imidacloprid, acetamiprid, thiamethoxam, chlorantraniliprole, cyantraniliprole, bensultap, cyhalothrin, cypermethrin, permethrin, deltamethrin, bifenthrin, lambda-cyhalothrin, thiacloprid, nitenpyram, buprofezin, pymetrozine, profenofos, chromafenozide, tebufenozide, thiocyclam, cartap, lepimectin, emamectin benzoate, pirimicarb, indoxacarb, carbofuran, carbosulfan, flufenoxuron, pyriproxyfen, flubendiamide, spirotetramat, novaluron, thiosultap-disodium, metaflumizone, 3-bromo-N-(2-bromo-4-chloro-6-(1-cyclopropylethylcarbamoyl)phenyl)-1-(3-chloropyridin-2-yl)-1H-pyrazol-5-carboxamide, 3-bromo-N-(4-chloro-2-(1-cyclopropylethylcarbamoyl)-6-methylphenyl)-1-(3-chloropyridin-2-yl)-1H-pyrazol-5-carboxamide, 3-bromo-N-(2-bromo-4-chloro-6-(cyclopropylmethylcarbamoyl)phenyl)-1-(3-chloropyridin-2-yl)-1H-pyrazol-5-carboxamide, 3-bromo-N-(4-chloro-2-methyl-6-(methylcarbamoyl)phenyl)-1-(3-chloropyridin-2-yl)-1H-pyrazol-5-carboxamide and 3-bromo-1-(3-chloropyridin-2-yl)-N-(4-cyano-2-methyl-6-(methylcarbamoyl)phenyl)-1H-pyrazol-5-carboxamide, validamycin, oryzastrobin, tricyclazole, isotianil, tiadinil, probenazole, flutolanil, pencycuron, isoprothiolane, thifluzamide, azoxystrobin, metominostrobin, ferimzone, fthalide, mepronil, diclomezine, pyroquilon and furametpyr may be mentioned.

Among the compounds of group X, further preferred are the following ones.

The insecticidal compounds include abamectin, fenobucarb, isoprocarb, chlorfluazuron, chlorantraniliprole, cyantraniliprole, chlorpyrifos, fipronil, clothianidin, spinetoram, spinosad, dinotefuran, methoxyfenozide, ethofenprox, ethiprole, acephate, benfuracarb, monocrotophos, silafluofen, imidacloprid, acetamiprid, thiamethoxam, thiosultap-disodium, metaflumizone, 3-bromo-N-(2-bromo-4-chloro-6-(1-cyclopropylethylcarbamoyl)phenyl)-1-(3-chloropyridin-2-yl)-1H-pyrazol-5-carboxamide, 3-bromo-N-(4-chloro-2-(1-cyclopropylethylcarbamoyl)-6-methylphenyl)-1-(3-chloropyridin-2-yl)-1H-pyrazol-5-carboxamide, 3-bromo-N-(2-bromo-4-chloro-6-(cyclopropylmethylcarbamoyl)phenyl)-1-(3-chloropyridin-2-yl)-1H-pyrazol-5-carboxamide, 3-bromo-N-(4-chloro-2-methyl-6-(methylcarbamoyl)phenyl)-1-(3-chloropyridin-2-yl)-1H-pyrazol-5-carboxamide and 3-bromo-1-(3-chloropyridin-2-yl)-N-(4-cyano-2-methyl-6-(methylcarbamoyl)phenyl)-1H-pyrazol-5-carboxamide.

The fungicidal compounds include oryzastrobin, tricyclazole, isotianil, tiadinil, probenazole, flutolanil, pencycuron, furametpyr and validamycin.

Among them, particularly preferred are chlorfluazuron, abamectin, fenobucarb, isoprocarb and validamycin.

The amount of the active ingredient compounds other than the agricultural compound of the above (a) to be used in the suspension of the present invention is usually from 0.1 to 60 wt %, preferably from 1 to 60 wt %.

Now, some preferred embodiments of the suspension of the present invention will be exemplified, but it should be understood that the present invention is by no means thereby restricted.

(1) A water-based pesticidal suspension comprising (a) an agricultural chemical or its salt having an aqueous solubility of from 500 mg/L to 6,000 mg/L at 20° C., (b) a polycarboxylate type surfactant, (c) a sulfonate type surfactant, and (d) water.

(2) The water-based pesticidal suspension according to (1), wherein the agricultural chemical (a) is an agricultural chemical having an aqueous solubility of from 3,000 mg/L to 6,000 mg/L at 20° C.

(3) The water-based pesticidal suspension according to (1) or (2), wherein the agricultural chemical (a) is at least one member selected from the group consisting of pirimicarb, thiamethoxam and flonicamid.

(4) The water-based pesticidal suspension according to (3), wherein the agricultural chemical (a) is flonicamid.

(5) The water-based pesticidal suspension according to (1), wherein the agricultural chemical (a) has an average particle size (volume) of from 0.5 μm to 10 μm.

(6) The water-based pesticidal suspension according to (1), wherein the polycarboxylate type surfactant (b) is a polycarboxylate.

(7) The water-based pesticidal suspension according to (1), wherein the sulfonate type surfactant (c) is at least one member selected from the group consisting of an alkyl sulfosuccinate, a lignosulfonate, a $C_{8-18}$ alkyl benzene sulfonate and a $C_{8-18}$ alkyl diphenyl ether disulfonate.

(8) The water-based pesticidal suspension according to (7), wherein the sulfonate type surfactant (c) is a lignosulfonate.

(9) The water-based pesticidal suspension according to (7), wherein the sulfonate type surfactant (c) is a lignosulfonate and an alkyl sulfosuccinate.

(10) The water-based pesticidal suspension according to (1), which contains an additive in addition to (a), (b), (c) and (d).

(11) The water-based pesticidal suspension according to (10), wherein the additive is at least one member selected from the group consisting of an antifreezing agent, a thickener, an antifoaming agent, an antiseptic agent, a pH modifier and a stabilizer.

(12) The water-based pesticidal suspension according to (10), wherein the additive is an antifreezing agent, a thickener and/or an antifoaming agent.

(13) The water-based pesticidal suspension according to (1), which further contains at least one agricultural chemical selected from the group consisting of an insecticidal compound and a fungicidal compound.

(14) The water-based pesticidal suspension according to (13), wherein said at least one member selected from the group consisting of an insecticidal compound and a fungicidal compound is the above-mentioned compounds of group X.

(15) The water-based pesticidal suspension according to (14), wherein said at least one compound selected from the group consisting of an insecticidal compound and a fungicidal compound is chlorfluazuron, abamectin, fenobucarb, isoprocarb and validamycin

(16) A method which comprises stabilizing the suspension state of an agricultural chemical or its salt having an aqueous solubility of from 500 mg/L to 6,000 mg/L at 20° C. in a water-based pesticidal suspension by means of (b) a polycarboxylate type surfactant and (c) a sulfonate type surfactant.

(17) A method which comprises stabilizing the suspension state of an agricultural chemical or its salt having an aqueous solubility of from 3,000 mg/L to 6,000 mg/L at 20° C. in a water-based pesticidal suspension by means of (b) a polycarboxylate type surfactant and (c) a sulfonate type surfactant.

EXAMPLES

Now, Examples of the present invention will be described, but it should be understood that the present invention is by no means thereby restricted.

Example 1

| | | | |
|---|---|---|---|
| (1) (a) | Flonicamid (purity: 97.5%) | 41.0 | parts by weight |
| (2) (b) | Polycarboxylate (tradename: Geropon T/36, manufactured by Rhodia) | 3.0 | parts by weight |
| (3) (c) | Lignosulfonate (tradename: SANX C, manufactured by NIPPON PAPER CHEMICALS Co., LTD.) | 5.0 | parts by weight |
| (4) (c) | Alkyl sulfosuccinate (tradename: New Kargen EP-70G, manufactured by TAKEMOTO OIL & FAT Co., LTD.) | 1.0 | part by weight |
| (5) | Propylene glycol | 7.0 | parts by weight |
| (6) | Aluminum magnesium silicate (tradename: Veegum R, manufactured by Sanyo Chemical Industries, Ltd.) | 0.2 | part by weight |
| (7) | Silicone type antifoaming agent (tradename: Rhodorsil Antifoam 432, manufactured by Rhodia Nicca Ltd.) | 0.5 | part by weight |
| (8) (d) | Water | 42.3 | parts by weight |

The above (1) and (2) to (8) were mixed, followed by wet grinding by DYNO-MILL (manufactured by SHINMARU ENTERPRISES CORPORATION) to obtain a water-based pesticidal suspension.

Example 2

| | | | |
|---|---|---|---|
| (1) (a) | Flonicamid (purity: 97.5%) | 27.4 | parts by weight |
| (2) (b) | Geropon T/36 (tradename) | 1.8 | parts by weight |
| (3) (c) | SANX C (tradename) | 4.4 | parts by weight |
| (4) (c) | New Kargen EP-70G (tradename) | 0.9 | part by weight |
| (5) | Propylene glycol | 6.2 | parts by weight |
| (6) | Veegum R (tradename) | 0.4 | part by weight |
| (7) | Xanthan gum (tradename: Rhodopol 23, manufactured by Rhodia) | 0.1 | part by weight |
| (8) | Rhodorsil Antifoam 432 (tradename) | 0.4 | part by weight |
| (9) | Proxel GXL (tradename, manufactured by Zeneca AG) | 0.1 | part by weight |
| (10) (d) | Water | 58.3 | parts by weight |

The above (1) and (2) to (10) were mixed, followed by wet grinding by DYNO-MILL (the same above) to obtain a water-based pesticidal suspension.

Example 3

| | | | |
|---|---|---|---|
| (1) (a) | Flonicamid (purity: 97.5%) | 19.0 | parts by weight |
| (2) (b) | Geropon T/36 (tradename) | 1.8 | parts by weight |
| (3) (c) | SANX C (tradename) | 4.6 | parts by weight |
| (4) (c) | New Kargen EP-70G (tradename) | 0.9 | part by weight |
| (5) | Propylene glycol | 6.4 | parts by weight |
| (6) | Veegum R (tradename) | 0.5 | part by weight |
| (7) | Rhodopol 23 (tradename) | 0.1 | part by weight |
| (8) | Rhodorsil Antifoam 432 (tradename) | 0.5 | part by weight |
| (9) | Proxel GXL (tradename) | 0.1 | part by weight |
| (10) (d) | Water | 66.1 | parts by weight |

The above (1) and (2) to (10) were mixed, followed by stirring and wet grinding by DYNO-MILL (the same above) to obtain a water-based pesticidal suspension.

Example 4

| | | | |
|---|---|---|---|
| (1) (a) | Flonicamid (purity: 97.5%) | 27.4 | parts by weight |
| (2) (b) | Geropon T/36 (tradename) | 1.8 | parts by weight |
| (3) (c) | SANX C (tradename) | 4.4 | parts by weight |
| (4) | Propylene glycol | 6.2 | parts by weight |
| (5) | Veegum R (tradename) | 0.4 | part by weight |
| (6) | Rhodopol 23 (tradename) | 0.1 | part by weight |
| (7) | Rhodorsil Antifoam 432 (tradename) | 0.4 | part by weight |
| (8) | Proxel GXL (tradename) | 0.1 | part by weight |
| (9) (d) | Water | 59.2 | parts by weight |

The above (1) and (2) to (9) were mixed, followed by wet grinding by DYNO-MILL (the same above) to obtain a water-based pesticidal suspension.

Example 5

| | | | |
|---|---|---|---|
| (1) (a) | Flonicamid (purity: 97.5%) | 1.0 | part by weight |
| (2) (b) | Geropon T/36 (tradename) | 0.5 | part by weight |
| (3) (c) | SANX C (tradename) | 20.0 | parts by weight |
| (4) | Propylene glycol | 6.2 | parts by weight |
| (5) | Veegum R (tradename) | 0.4 | part by weight |
| (6) | Rhodopol 23 (tradename) | 0.1 | part by weight |
| (7) | Rhodorsil Antifoam 432 (tradename) | 0.4 | part by weight |
| (8) | Proxel GXL (tradename) | 0.1 | part by weight |
| (9) (d) | Water | 71.3 | parts by weight |

The above (1) and (2) to (9) are mixed, followed by wet grinding by DYNO-MILL (the same above) to obtain a water-based pesticidal suspension.

Example 6

| | | | |
|---|---|---|---|
| (1) (a) | Flonicamid (purity: 97.5%) | 60.0 | parts by weight |
| (2) (b) | Geropon T/36 (tradename) | 10.0 | parts by weight |
| (3) (c) | SANX C (tradename) | 1.0 | parts by weight |
| (4) | Propylene glycol | 1.2 | parts by weight |
| (5) | Veegum R (tradename) | 0.4 | part by weight |
| (6) | Rhodopol 23 (tradename) | 0.1 | part by weight |
| (7) | Rhodorsil Antifoam 432 (tradename) | 0.4 | part by weight |
| (8) | Proxel GXL (tradename) | 0.1 | part by weight |
| (9) (d) | Water | 26.8 | parts by weight |

The above (1) and (2) to (9) are mixed, followed by wet grinding by DYNO-MILL (the same above) to obtain a water-based pesticidal suspension.

Comparative Example 1

| | | | |
|---|---|---|---|
| (1) (a) | Flonicamid (purity: 97.5%) | 41.0 | parts by weight |
| (2) | Potassium salt of polyoxyethylene-tristyryl phenyl ether phosphoric acid ester (tradename: Soprophor FLK/70, manufactured by Rhodia Nicca Ltd.) | 5.0 | parts by weight |
| (3) | Propylene glycol | 7.0 | parts by weight |
| (4) | Veegum R (tradename) | 0.5 | part by weight |
| (5) | Rhodopol 23 (tradename) | 0.03 | part by weight |

| | | |
|---|---|---|
| (6) | Rhodorsil Antifoam 432 (tradename) | 0.5 part by weight |
| (7) | Proxel GXL (tradename) | 0.03 part by weight |
| (8) (d) | Water | 45.94 parts by weight |

The above (1) and (2) to (8) were mixed, followed by wet grinding by DYNO-MILL (the same above) to obtain a water-based pesticidal suspension.

Comparative Example 2

| | | |
|---|---|---|
| (1) (a) | Flonicamid (purity: 97.5%) | 41.0 parts by weight |
| (2) | Potassium salt of polyoxyethylene-tristyryl phenyl ether phosphoric acid ester (tradename: Soprophor FLK/70, manufactured by Rhodia Nicca Ltd.) | 3.0 parts by weight |
| (3) (c) | New Kargen EP-70G (tradename) | 0.3 part by weight |
| (4) | Propylene glycol | 7.0 parts by weight |
| (5) | Veegum R (tradename) | 0.5 part by weight |
| (6) | Rhodopol 23 (tradename) | 0.03 part by weight |
| (7) | Rhodorsil Antifoam 432 (tradename) | 0.5 part by weight |
| (8) | Proxel GXL (tradename) | 0.03 part by weight |
| (9) (d) | Water | 47.64 parts by weight |

The above (1) and (2) to (9) were mixed, followed by wet grinding by DYNO-MILL (the same above) to obtain a water-based pesticidal suspension.

Comparative Example 3

| | | |
|---|---|---|
| (1) (a) | Flonicamid (purity: 97.5%) | 41.0 parts by weight |
| (2) (b) | Geropon T/36 (tradename) | 5.0 parts by weight |
| (3) | Propylene glycol | 7.0 parts by weight |
| (4) | Veegum R (tradename) | 0.2 part by weight |
| (5) | Rhodorsil Antifoam 432 (tradename) | 0.5 part by weight |
| (6) (d) | Water | 46.3 parts by weight |

The above (1) and (2) to (6) were mixed, followed by wet grinding by DYNO-MILL (the same above) to obtain a water-based pesticidal suspension.

Example 7

| | | |
|---|---|---|
| (1) (a) | Pirimicarb | 27.0 parts by weight |
| (2) (b) | Geropon T/36 (tradename) | 1.8 parts by weight |
| (3) (c) | SANX C (tradename) | 4.5 parts by weight |
| (4) (c) | New Kargen EP-70G (tradename) | 0.9 part by weight |
| (5) | Propylene glycol | 6.3 parts by weight |
| (6) | Veegum R (tradename) | 0.4 part by weight |
| (7) | Rhodopol 23 (tradename) | 0.1 part by weight |
| (8) | Rhodorsil Antifoam 432 (tradename) | 0.4 part by weight |
| (9) | Proxel GXL (tradename) | 0.1 part by weight |
| (10) (d) | Water | 58.5 parts by weight |

The above (1) and (2) to (10) were mixed, followed by wet grinding by DYNO-MILL (the same above) to obtain a water-based pesticidal suspension.

Example 8

| | | |
|---|---|---|
| (1) (a) | Thiamethoxam | 27.0 parts by weight |
| (2) (b) | Geropon T/36 (tradename) | 1.8 parts by weight |
| (3) (c) | SANX C (tradename) | 4.5 parts by weight |
| (4) (c) | New Kargen EP-70G (tradename) | 0.9 part by weight |
| (5) | Propylene glycol | 6.3 parts by weight |
| (6) | Veegum R (tradename) | 0.4 part by weight |
| (7) | Rhodopol 23 (tradename) | 0.1 part by weight |
| (8) | Rhodorsil Antifoam 432 (tradename) | 0.4 part by weight |
| (9) | Proxel GXL (tradename) | 0.1 part by weight |
| (10) (d) | Water | 58.5 parts by weight |

The above (1) and (2) to (10) were mixed, followed by wet grinding by DYNO-MILL (the same above) to obtain a water-based pesticidal suspension.

Example 9

| | | |
|---|---|---|
| (1) (a) | Flonicamid (purity: 97.5%) | 18.2 parts by weight |
| (2) | Chlorfluazuron | 4.4 parts by weight |
| (3) (b) | Geropon T/36 (tradename) | 1.8 parts by weight |
| (4) (c) | SANX C (tradename) | 4.6 parts by weight |
| (5) (c) | New Kargen EP-70G (tradename) | 0.9 part by weight |
| (6) | Propylene glycol | 6.4 parts by weight |
| (7) | Veegum R (tradename) | 0.5 part by weight |
| (8) | Rhodopol 23 (tradename) | 0.1 part by weight |
| (9) | Rhodorsil Antifoam 432 (tradename) | 0.5 part by weight |
| (10) | Proxel GXL (tradename) | 0.1 part by weight |
| (11) (d) | Water | 62.5 parts by weight |

The above (1) and (2) to (11) were mixed, followed by wet grinding by DYNO-MILL (the same above) to obtain a water-based pesticidal suspension.

According to the present invention, as shown below, even if the agricultural chemical (a) is blended with another active ingredient, it is possible to obtain a stable water-based suspension.

Example 10

| | | |
|---|---|---|
| (1) (a) | Flonicamid (purity: 97.5%) | 27.2 parts by weight |
| (2) | Abamectin | 2.7 parts by weight |
| (3) (b) | Geropon T/36 (tradename) | 1.8 parts by weight |
| (4) (c) | SANX C (tradename) | 4.6 parts by weight |
| (5) (c) | New Kargen EP-70G (tradename) | 0.9 part by weight |
| (6) | Propylene glycol | 6.4 parts by weight |
| (7) | Veegum R (tradename) | 0.5 part by weight |
| (8) | Rhodopol 23 (tradename) | 0.1 part by weight |
| (9) | Rhodorsil Antifoam 432 (tradename) | 0.5 part by weight |
| (10) | Proxel GXL (tradename) | 0.1 part by weight |
| (11) (d) | Water | 55.2 parts by weight |

The above (1) and (2) to (11) are mixed, followed by wet grinding to obtain a water-based pesticidal suspension of the present invention.

Example 11

| | | |
|---|---|---|
| (1) (a) | Flonicamid (purity: 97.5%) | 4.5 parts by weight |
| (2) | Isoprocarb | 22.1 parts by weight |
| (3) (b) | Geropon T/36 (tradename) | 1.8 parts by weight |
| (4) (c) | SANX C (tradename) | 4.6 parts by weight |
| (5) (c) | New Kargen EP-70G (tradename) | 0.9 part by weight |
| (6) | Propylene glycol | 6.4 parts by weight |
| (7) | Veegum R (tradename) | 0.5 part by weight |
| (8) | Rhodopol 23 (tradename) | 0.1 part by weight |
| (9) | Rhodorsil Antifoam 432 (tradename) | 0.5 part by weight |
| (10) | Proxel GXL (tradename) | 0.1 part by weight |
| (11) (d) | Water | 58.5 parts by weight |

The above (1) and (2) to (11) are mixed, followed by wet grinding to obtain a water-based pesticidal suspension of the present invention.

Example 12

| | | | |
|---|---|---|---|
| (1) (a) | Flonicamid (purity: 97.5%) | 4.5 | parts by weight |
| (2) | Fenobucarb | 22.1 | parts by weight |
| (3) (b) | Geropon T/36 (tradename) | 1.8 | parts by weight |
| (4) (c) | SANX C (tradename) | 4.6 | parts by weight |
| (5) (c) | New Kargen EP-70G (tradename) | 0.9 | part by weight |
| (6) | Propylene glycol | 6.4 | parts by weight |
| (7) | Veegum R (tradename) | 0.5 | part by weight |
| (8) | Rhodopol 23 (tradename) | 0.1 | part by weight |
| (9) | Rhodorsil Antifoam 432 (tradename) | 0.5 | part by weight |
| (10) | Proxel GXL (tradename) | 0.1 | part by weight |
| (11) (d) | Water | 58.5 | parts by weight |

The above (1) and (2) to (11) are mixed, followed by wet grinding to obtain a water-based pesticidal suspension of the present invention.

Example 13

| | | | |
|---|---|---|---|
| (1) (a) | Flonicamid (purity: 97.5%) | 11.6 | parts by weight |
| (2) | Validamycin | 17.7 | parts by weight |
| (3) (b) | Geropon T/36 (tradename) | 1.8 | parts by weight |
| (4) (c) | SANX C (tradename) | 4.6 | parts by weight |
| (5) (c) | New Kargen EP-70G (tradename) | 0.9 | part by weight |
| (6) | Propylene glycol | 6.4 | parts by weight |
| (7) | Veegum R (tradename) | 0.5 | part by weight |
| (8) | Rhodopol 23 (tradename) | 0.1 | part by weight |
| (9) | Rhodorsil Antifoam 432 (tradename) | 0.5 | part by weight |
| (10) | Proxel GXL (tradename) | 0.1 | part by weight |
| (11) (d) | Water | 55.8 | parts by weight |

The above (1) and (2) to (11) are mixed, followed by wet grinding to obtain a water-based pesticidal suspension of the present invention.

Example 14

| | | | |
|---|---|---|---|
| (1) (a) | Flonicamid (purity: 97.5%) | 10.3 | parts by weight |
| (2) | At least one member selected from the above-mentioned Group X | 10.0 | parts by weight |
| (3) (b) | Geropon T/36 (tradename) | 1.8 | parts by weight |
| (4) (c) | SANX C (tradename) | 4.6 | parts by weight |
| (5) (c) | New Kargen EP-70G (tradename) | 0.9 | part by weight |
| (6) | Propylene glycol | 6.4 | parts by weight |
| (7) | Veegum R (tradename) | 0.5 | part by weight |
| (8) | Rhodopol 23 (tradename) | 0.1 | part by weight |
| (9) | Rhodorsil Antifoam 432 (tradename) | 0.5 | part by weight |
| (10) | Proxel GXL (tradename) | 0.1 | part by weight |
| (11) (d) | Water | 64.8 | parts by weight |

The above (1) and (2) to (11) are mixed, followed by wet grinding to obtain a water-based pesticidal suspension of the present invention.

Test Example 1

Initial Physical Property Tests

The water-based pesticidal suspension obtained in each of Examples 1 to 4, 7 and 9 and Comparative Examples 1 to 3 was filled in a 30 mL glass bottle, which was capped and then immersed in a constant temperature water tank at 20° C. 30 Minutes later, the glass bottle was taken out, and the viscosity of the water-based pesticidal suspension was measured by means of a B type viscosimeter (rotor: No. 2, rotational speed of rotor: 60 rpm). Further, the average particle size (volume) was measured by a particle size analyzer Microtrac HRA (manufactured by NIKKISO Co., Ltd.). The results are shown in Tables 1, 2 and 3.

Test Example 2

Suspension Stability Test after Heating (54° C. for 2 Weeks)

The water-based pesticidal suspension was filled in a 30 mL glass bottle, which was capped and then stored in an incubator at 54° C. for 2 weeks, whereupon the glass bottle was taken out from the constant temperature machine, and visual observation of the suspension state, and the viscosity measurement and particle size measurement in the same manner as in Test Example 1 were carried out. The visual observation was assessed by means of eye observation or optical microscopic observation (600 magnification, OLYMPUS CORPORATION, BH-2). Here, presence or absence of coarse particles was assessed by determining the existence of crystals by means of eye observation, or by determining the existence of crystals of 50 μm or more exist, by means of optical microscopic observation. The results are also shown in Tables 1, 2 and 3.

Test Example 3

Suspension Stability Test after Storage at Room Temperature (Room Temperature for 2 Years)

The water-based pesticidal suspension was filled in a 30 mL glass bottle, which was capped and then stored in a laboratory for 2 years, whereupon visual observation of the suspension state, and the viscosity measurement and the particle size measurement in the same manner as in Test Example 1, were carried out. The results are also shown in Table 1.

It is evident that the water-based pesticidal suspension of the present invention was excellent in suspension stability, and the physical properties in the formulation were stable such that the suspension state was stabilized, no coarse particles were precipitated, and the average particle size of the active ingredient particles and the viscosity of the suspension undergo no change even under severe conditions such as storage by heating condition or storage for a long period of time.

On the other hand, in the suspension stability test after heating and the suspension stability ordinary temperature evaluation test, in Comparative Examples 1 and 2, the entire suspension underwent gelation, and in Comparative Example 3, the suspension underwent phase separation to a supernatant layer and a suspension layer, and in the vicinity of the interface, needle coarse particles were precipitated, and the form of the desired suspension was not maintained, and thus, it is evident that in case component (b) and component (c) are not contained at the same time, it is not possible to obtain a water-based pesticidal suspension having a storage stability for a long period of time.

TABLE 1

| | | Ex. 1 | Ex. 2 | Ex. 3 | Ex. 4 | Comp. Ex. 1 | Comp. Ex. 2 | Comp. Ex. 3 |
|---|---|---|---|---|---|---|---|---|
| Test Example 1 Initial physical properties | Average particle size (μm) | 2.9 | 1.7 | 1.1 | 1.6 | 4.9 | 5.0 | 8.3 |
| | Viscosity (mPa·s) | 420 | 240 | 240 | 240 | 360 | 380 | 400 |
| Test Example 2 Suspension stability (heating test) | Appearance | No coarse particles were observed in suspension. | No coarse particles were observed in suspension. | No coarse particles were observed in suspension. | No coarse particles were observed in suspension. | Entire suspension gelled. | Entire suspension gelled. | Coarse needle-form particles precipitated in the vicinity of the interface between the suspension layer and the supernatant layer. |
| | Average particle size (μm) | 3.2 | 2.0 | 1.5 | 1.9 | — | — | — |
| | Viscosity (mPa·s) | 400 | 220 | 210 | 220 | — | — | — |
| Test Example 3 Suspension stability (ordinary temperature test) | Appearance | No coarse particles were observed in suspension. | No coarse particles were observed in suspension. | — | — | Entire suspension gelled. | Entire suspension gelled. | — |
| | Average particle size (μm) | 2.1 | 1.9 | — | — | — | — | — |
| | Viscosity (mPa·s) | 480 | 220 | — | — | — | — | — |

TABLE 2

| | | Ex. 7 | Ex. 8 |
|---|---|---|---|
| Test Example 1 Initial physical properties | Average particle size (μm) | 2.9 | 8.4 |
| | Viscosity (mPa·s) | 112 | 122 |
| Test Example 2 Suspension stability (heating test) | Appearance | No coarse particles were observed in suspension. | No coarse particles were observed in suspension. |
| | Average particle size (μm) | 2.6 | 7.5 |
| | Viscosity (mPa·s) | 213 | 132 |

TABLE 3

| | | Ex. 9 |
|---|---|---|
| Test Example 1 Initial physical properties | Average particle size (μm) | 1.4 |
| | Viscosity (mPa·s) | 200 |
| Test Example 2 Suspension stability (heating test) | Appearance | No coarse particles were observed in suspension. |
| | Average particle size (μm) | 1.6 |
| | Viscosity (mPa·s) | 180 |

The entire disclosure of Japanese Patent Application No. 2010-157295 filed on Jul. 9, 2010 including specification, claims and summary is incorporated herein by reference in its entirety.

The invention claimed is:

1. A water-based pesticidal suspension consisting of:
 (a) flonicamid;
 (b) a polycarboxylate surfactant;
 (c) a sulfonate surfactant which is at least one member selected from the group consisting of an alkyl sulfosuccinate, a lignosulfonate, a $C_{8-18}$ alkyl benzene sulfonate and a $C_{8-18}$ alkyl diphenyl ether disulfonate;
 (d) water;
 (e) optionally at least one agent selected from the group consisting of an antifreezing agent, a thickener, an antifoaming agent, an antiseptic agent, and a pH modifier; and
 (f) optionally at least one additive selected from the group consisting of an additional insecticidal compound and a fungicidal compound.

2. The water-based pesticidal suspension according to claim 1, wherein an average particle size of the volume distribution of (a) flonicamid is from 0.5 μm to 10 μm.

3. The water-based pesticidal suspension according to claim 1, wherein the polycarboxylate surfactant (b) is a sodium salt of maleic acid/olefin copolymer.

4. The water-based pesticidal suspension according to claim 1, wherein the sulfonate surfactant (c) is a lignosulfonate.

5. The water-based pesticidal suspension according to claim 1, wherein the sulfonate surfactant (c) is a lignosulfonate and an alkyl sulfosuccinate.

6. The water-based pesticidal suspension according to claim 1, wherein the at least one agent (e) is present.

7. The water-based pesticidal suspension according to claim 1, wherein the at least one additive (f) is present.

8. The water-based pesticidal suspension according to claim 1, wherein the polycarboxylate surfactant (b) is a sodium salt of maleic acid/olefin copolymer, and the sulfonate surfactant (c) is a lignosulfonate.

9. The water-based pesticidal suspension according to claim 1, wherein the content of flonicamid (a) in the water-based pesticidal suspension is from 0.1 to 90 wt %.

10. The water-based pesticidal suspension according to claim 1, wherein the content of flonicamid (a) in the water-based pesticidal suspension is from 1 to 60 wt %.

11. The water-based pesticidal suspension according to claim 1, wherein the content of flonicamid (a) in the water-based pesticidal suspension is from 5 to 45 wt %.

12. The water-based pesticidal suspension according to claim 1, wherein the weight ratio of the polycarboxylate surfactant (b) to the sulfonate surfactant (c) is from 1:0.01 to 1:200.

13. The water-based pesticidal suspension according to claim 1, wherein the weight ratio of the polycarboxylate surfactant (b) to the sulfonate surfactant (c) is from 1:0.01 to 1:40.

* * * * *